(12) United States Patent
de la Torre et al.

(10) Patent No.: US 7,044,947 B2
(45) Date of Patent: May 16, 2006

(54) POLYPECTOMY DEVICE AND METHOD

(75) Inventors: Roger A. de la Torre, Saratoga, CA (US); Kenneth H. Mollenauer, Saratoga, CA (US)

(73) Assignee: Starion Instruments Corporation, Saratoga, CA (US)

( * ) Notice: Subject to any disclaimer, the term of this patent is extended or adjusted under 35 U.S.C. 154(b) by 42 days.

(21) Appl. No.: 10/658,226

(22) Filed: Sep. 8, 2003

(65) Prior Publication Data

US 2004/0044335 A1 Mar. 4, 2004

Related U.S. Application Data

(63) Continuation of application No. 09/917,104, filed on Jul. 27, 2001, now Pat. No. 6,616,659.

(51) Int. Cl.
*A61B 18/18* (2006.01)
(52) U.S. Cl. .......................... 606/28; 128/898
(58) Field of Classification Search ............... 606/47, 606/32–34, 39–40, 41, 46, 27–52
See application file for complete search history.

(56) References Cited

U.S. PATENT DOCUMENTS

| | | | |
|---|---|---|---|
| 3,829,903 A * | 8/1974 | Stati et al. ................. 600/36 |
| 4,326,530 A * | 4/1982 | Fleury, Jr. .................. 606/47 |
| 4,493,320 A | 1/1985 | Treat ..................... 128/303.15 |
| 5,122,147 A * | 6/1992 | Sewell, Jr. ................. 606/110 |
| 5,318,564 A | 6/1994 | Eggers ........................ 606/47 |
| 5,437,665 A | 8/1995 | Munro ........................ 606/47 |
| 5,565,122 A | 10/1996 | Zinnbauer et al. ........... 606/47 |
| 5,746,747 A | 5/1998 | McKeating ................. 606/114 |
| 5,906,620 A | 5/1999 | Nakao et al. ............... 606/113 |
| 6,010,512 A * | 1/2000 | Chu et al. ................... 606/113 |
| 6,015,415 A | 1/2000 | Avellanet ................... 606/113 |
| 6,077,277 A | 6/2000 | Mollenauer et al. ........ 606/144 |
| 6,093,195 A * | 7/2000 | Ouchi ........................ 606/113 |
| 6,176,858 B1 | 1/2001 | Dequesne et al. ............ 606/47 |

\* cited by examiner

*Primary Examiner*—Roy D. Gibson
*Assistant Examiner*—Pete Vrettakos
(74) *Attorney, Agent, or Firm*—K. David Crockett, Esq.; Marc J. Frechette, Esq.; Crockett & Crockett

(57) ABSTRACT

A polypectomy device and method which includes a snare cable, a fixed jaw and a moveable jaw. The snare cable is routed through both the fixed jaw and the moveable jaw. The snare cable forms a hoop for encircling the polyp. Shortening the snare cable positions the jaws about the base of the polyp and further shortening the cable closes the jaws. The fixed jaw includes a heating element which cauterizes the base of the polyp. The closing of the jaws and the heating of the heating element cuts and seals the polyp.

6 Claims, 5 Drawing Sheets

POLYPECTOMY DEVICE AND METHOD

This application is a continuation of U.S. application Ser. No. 09/917,104 filed Jul. 27, 2001, now U.S. Pat. No. 6,616,659.

FIELD OF THE INVENTIONS

The invention relates general to medical devices, and more specifically to devices for performing a polypectomy.

BACKGROUND OF THE INVENTIONS

Polyps are defined as any growth or mass protruding from a mucous membrane. Polyps can occur wherever there is mucous membrane, namely, in the nose, ears, mouth, lungs, heart, stomach, intestines, urinary bladder, uterus, and cervix. Most polyps are benign growths that eventually stop growing. But some of these polyps keep growing. Genetic mutations can transform them into cancerous tumors. As these cancerous tumors grow larger, they continue growing and begin to burrow deeper and deeper into the tissue supporting the polyp. In the final stages the cancer invades the blood and lymph systems and the malignant cells of the tumor spread to other organs. The problem is particularly severe, yet readily treated, in the colon. Colorectal cancer is the second leading cause of death due to cancer in the United States. If the cancer is detected and treated in its early stages, it can be cured more than 90% of the time. Thus, early detection and removal of colorectal polyps, whether benign, pre-cancerous, or cancerous, is highly effective in avoiding or treating colorectal cancer.

Polyps may be attached to a mucous membrane by a thin stalk or the polyp may have a broad base. A polyp that is attached by a thin stalk is called a pedunculated polyp and a polyp that is attached by a broad base is called a sessile polyp. Various devices have been proposed for removing polyps, especially pedunculated polyps, from the body. For example, Avellanet, Polypectomy Snare Instrument, U.S. Pat. No. 6,015,415 (Jan. 18, 2000) teaches a polypectomy device using a snare loop connected to a power source to supply cautery current. The snare loop is used to capture the polyp and current is applied to the snare loop which cauterizes the polyp as the snare is closed tightly around the polyp. McKeating, Polypectomy Instrument, U.S. Pat. No. 5,746,747 (May 5, 1998) teaches a polypectomy device using grasping forceps to hold the polyp and a snare wire for cutting the polyp. Electrical current is supplied to the snare wire to cut and cauterize the polyp while the grasping forceps hold onto the body of the polyp. Nakao et al., Surgical Cauterization Snare with Ligating Suture, U.S. Pat. No. 5,906,620 (May 25, 1999) teaches using two snare loops. The first loop cauterizes the polyp while the second loop acts as a suture for ligating the polyp. The second loop is left behind in the colon.

SUMMARY

The present polypectomy device and method effectively removes polyps from the body. The device includes a first jaw and a second jaw. One of the jaws includes a heating element for cauterizing the tissue of the polyp. A snare cable is routed through each of the jaws. The snare cable forms a hoop for capturing the polyp. As the snare cable is pulled proximally it positions the jaws at the base or stalk of the polyp. As the snare cable is pulled further it closes the jaws. The closing of the jaws works in conjunction with a heating element to cut and seal the tissue between the jaws.

DETAILED DESCRIPTION OF THE INVENTIONS

Figure 1:
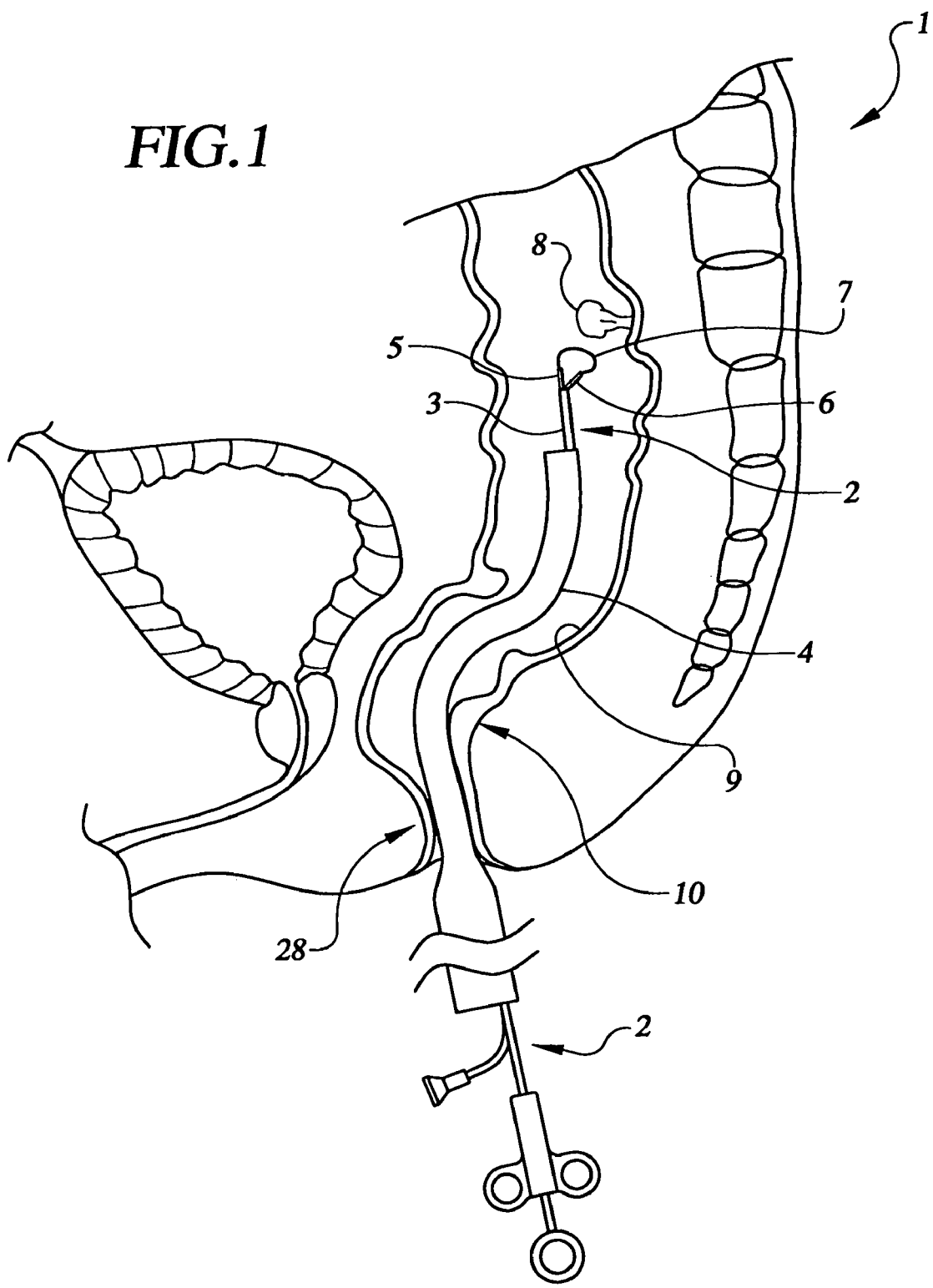
FIG. 1 is an overview of the polypectomy device inserted into the colon of a patient.

FIG. 1 shows an overview of the polypectomy device inserted into the colon of a patient 1. The polypectomy device 2 includes an elongated flexible catheter 3 extending out of the distal end of an endoscope 4. The distal end of the catheter includes a fixed jaw 5, a moveable jaw 6, and a snare cable 7. The snare cable may be operated to capture the polyp 8 and as the length of the snare cable is shortened, the polyp is drawn into the jaws and the moveable jaw is pulled toward the fixed jaw. The heating element 17 on the fixed jaw (See FIGS. 2 and 3) may be operated to necrose the tissue trapped between the jaws. The combination of heat and pressure causes the tissue to divide which severs the polyp from the colon wall 9 of the colon 10.

Figure 2:
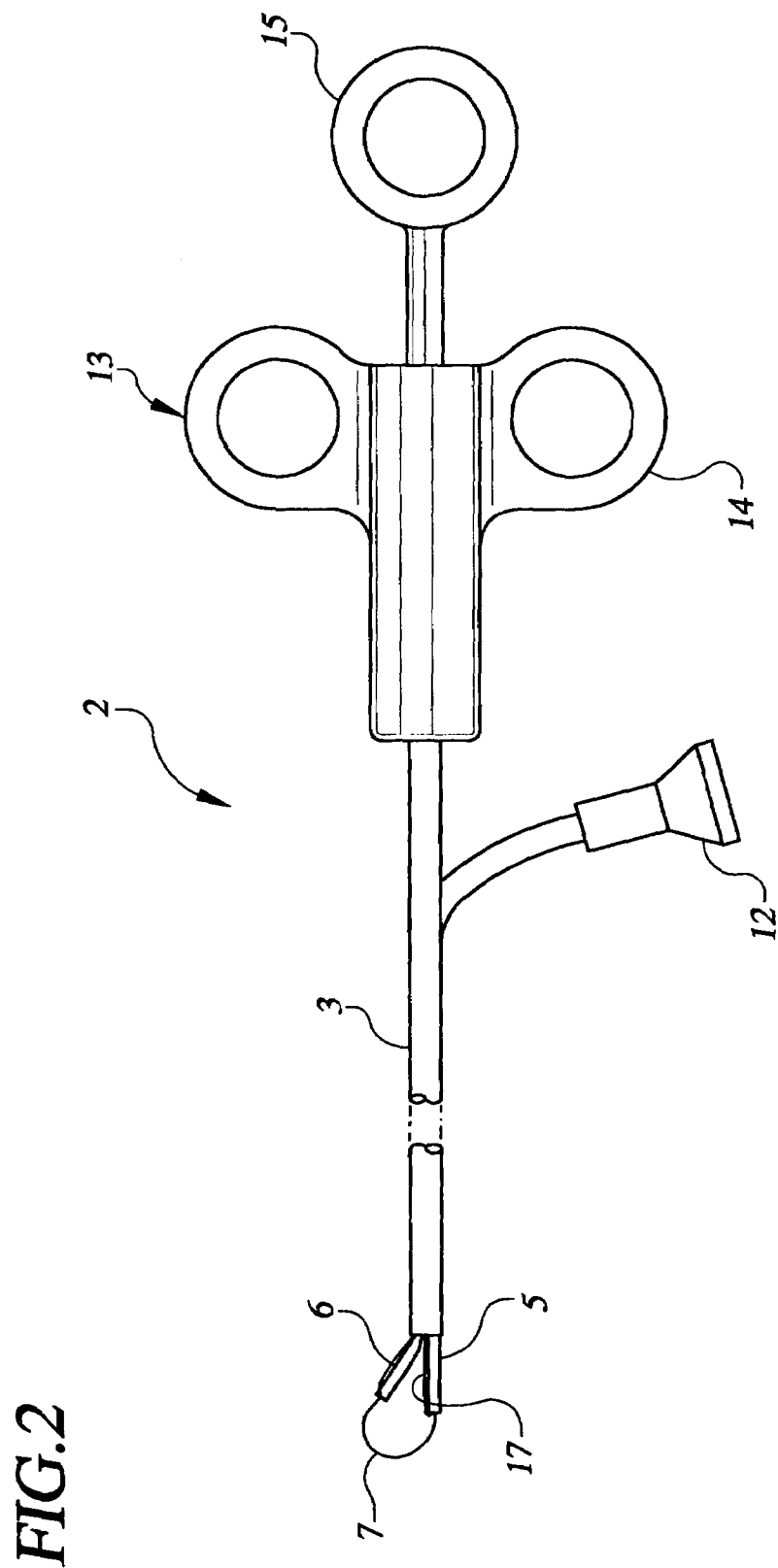
FIG. 2 is an overall side-view of the polypectomy device with a handle, an electrical connector, and a jaw assembly.

FIG. 2 shows an overall side-view of the polypectomy device 2. The proximal end of the device includes a two-wire electrical connector 12, and a handle 13. The two-wire electrical connector connects the catheter 3 to an electrical power source (not shown). The handle includes a cable trigger 14 and a fixed finger hold 15. The cable trigger may be operated to pull the snare cable 7, which captures the polyp and operates the moveable jaw 6. Closing the jaw assembly and activating the power source to heat the heating element 17 cuts the polyp and seals the tissue.

Figure 3:
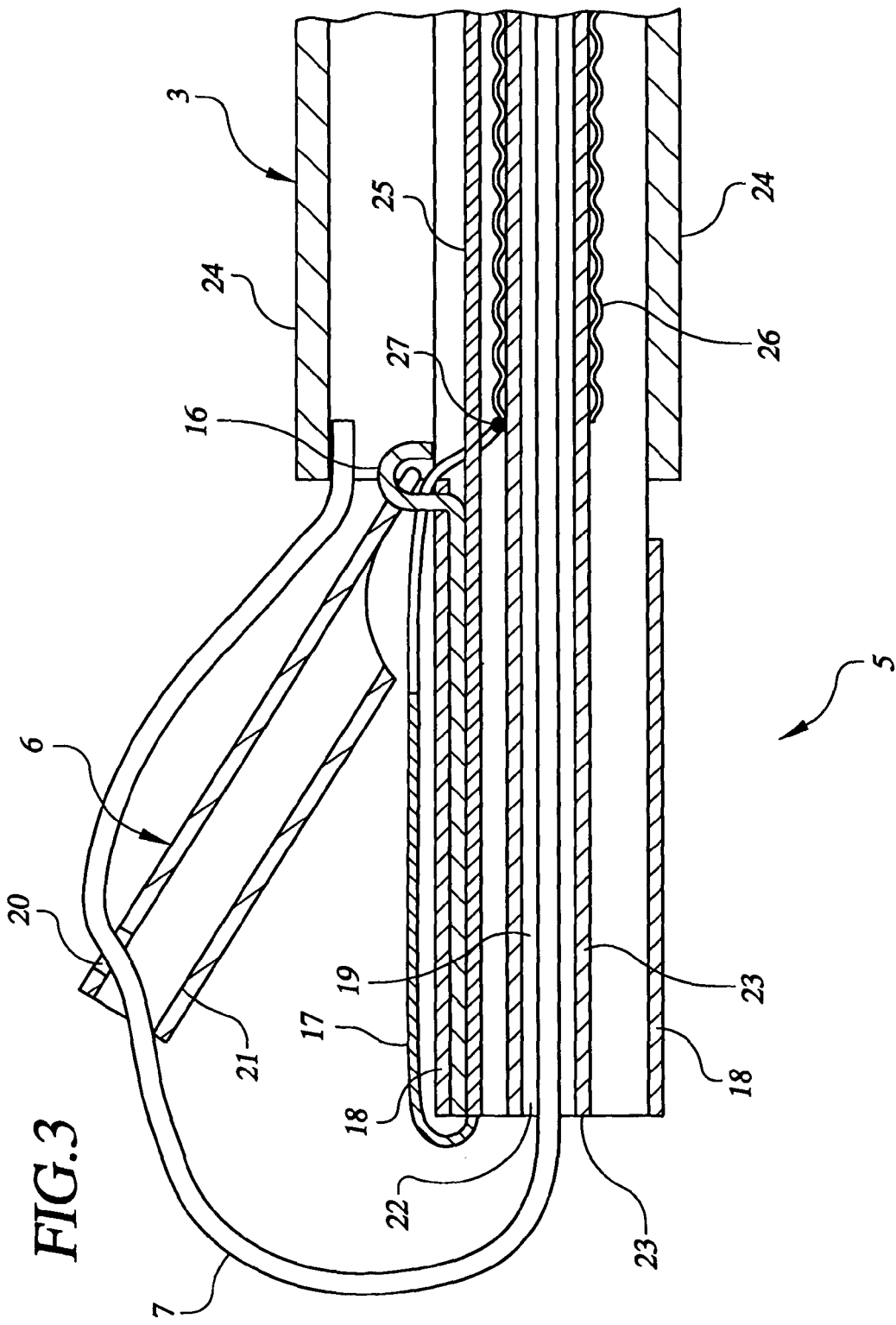
FIG. 3 is a close-up cross sectional view of the jaw assembly located on the distal end of the polypectomy device.

FIG. 3 is a close-up cross sectional view of the distal end of the polypectomy device. The snare cable 7, the fixed jaw 5 and the moveable jaw 6 extend out of the distal end of the catheter body 3. The fixed jaw is attached to the catheter body, and the moveable jaw is operatively connected to the catheter body at a hinge 16. It should be noted that while we have referred to a fixed jaw and a moveable jaw, both jaws may be moveable. Both jaws may be hinged to the catheter, or otherwise rotatable relative to each other and secured to the catheter.

The fixed jaw 5 includes a heating element 17, an insulation tube 18, and a lumen 19. The moveable jaw 6 includes a hole 20 (through which the snare cable passes) at its distal tip, a hinge 16 at its proximal end, and a silicone pad 21. A distal outlet 22 is formed by the lumen 19 of the fixed jaw extending completely through the fixed jaw. The fixed jaw and the moveable jaw close together in a scissor-like movement. The surfaces of the fixed jaw and the moveable jaw that fit together are the grasping faces. The silicone pad 21 of the moveable jaw is located along the grasping face of the moveable jaw and the portion of the insulation tube 18 facing the moveable jaw serves as the grasping face of the fixed jaw.

The fixed jaw and the moveable jaw can be composed of stainless steel or other suitable metal, plastic, or ceramic. The fixed jaw also includes an insulation tube that can be composed of polyamide, fluropolymer, or a PTFE/polyamide blend such as Xylan® (other insulative materials can be used). The insulation tube 18 isolates the heating element 17 from the stainless steel portion of the fixed jaw thereby preventing the heating element from heating the entire fixed jaw.

The heating element is composed of an electrically conductive material, such as nichrome, which is sufficiently resistive to heat up significantly when electricity is passed through it. The heating element can be approximately 1/10,000 nichrome wire having a length of approximately 10 mm. The power supply can generate approximately 3 to 30 watts of power, and the heating element approximately 2 to 7 watts of power. Alternative forms of heating elements may be used, such as ceramic heating elements, RF heating elements, and monopolar and bipolar heating elements. Additionally, heating elements may be placed on either jaw, or on both jaws.

The distal end of the snare cable 7 is fixed to the catheter body 3 and extends along the outside of the moveable jaw 6 through the hole 20 in the distal tip of the moveable jaw (though it may be fixed, at its terminus, to the distal tip of the moveable jaw). The cable then goes into the distal outlet 22 of the fixed jaw 5, through the lumen 19 to the cable trigger 14 located at the proximal end of the device. The lumen 19 of the fixed jaw includes a friction liner 23. The friction liner can be composed of nylon or Teflon®, which reduces the friction created by the snare cable 7 moving through the lumen of the fixed jaw, thereby permitting the snare cable to be operated smoothly and easily.

The fixed jaw 5 is formed as a cylindrical tube and the moveable jaw 6 is formed as a concave semicylindrical body that mates with the fixed jaw. The fixed jaw and the moveable jaw are fashioned similar to a curling iron for hair, which includes a cylindrical heated tube and a moveable semicylindrical jaw that fit together to curl hair. In the curling iron art the fixed jaw is called the barrel and the moveable jaw is called the clip, and they function in a similar manner as the fixed jaw and the moveable jaw in this device. Thus, by analogy, the fixed jaw may be referred to as a barrel, and the moveable jaw may be referred to as a clip.

The outer most layer of the catheter body is an insulated catheter jacket 24. Inside the catheter body are the electrical wire 25, the braided conductor 26, the lumen, and the snare cable 7. The electrical wire is connected to the distal end of the heating element 17, which is located on the grasping face of the fixed jaw, and supplies the electrical current from the electric source to the heating element. The current flows from the electric power source into the two-wire electrical connector 12 through the electrical wire 25 into the heating element 17. The current then flows from the heating element through the conductive crimp 27, located at the proximal end of the heating element, into the braided conductor 26 and back to the two-wire connector to complete the circuit. The braided conductor may be replaced with a wire if space permits.

In use, an endoscope is inserted into the patient's body to the area where the polyp is located. The endoscope is used to view inside the patient's body and look for polyps. If a polyp is found the surgeon inserts the polypectomy catheter into the working lumen of the endoscope. The surgeon then moves the distal end of the catheter toward the polyp and extends the snare cable to form a hoop which enables the surgeon to capture the polyp. The surgeon manually rotates the catheter such that the snare cable hoop can be properly oriented and placed over the polyp. The manual rotation of the catheter is accomplished by rotation of the handle.

Once the polyp is encompassed by the snare cable, the surgeon activates the cable trigger thereby drawing the snare cable proximally relative to the catheter and closing the loop about the polyp. As the surgeon pulls the snare cable, the fixed jaw and the moveable jaw are pulled into place on either side of the polyp. As the surgeon further shortens the snare cable, it operates the moveable jaw to draw it toward the fixed jaw, thereby pulling the jaws together. The electrical power source is activated, which heats the heating element located on the fixed jaw. Therefore, as the jaws are held closed, the heating element and the jaws work together to both cut and seal the tissue. The power source may be activated by a footswitch (not shown), or it may be operated by a switch or button located on the catheter or the power source. It may also be activated by a limit switch which is activated by the proximal movement of the cable trigger.

As discussed above, polyps form in mucous membrane, and mucous membranes exist in many areas of the body. Polyps can form in a patient's colon 10. One way of looking for polyps in a patient's colon is a colonoscopy. During a colonoscopy the surgeon inserts an endoscope 4 into the patient's colon through the patient's anus 28 (See FIG. 1). If a polyp 8 is found, the surgeon inserts the polypectomy device 2 into the working lumen of the endoscope and follows the procedure discussed above.

Figure 4:
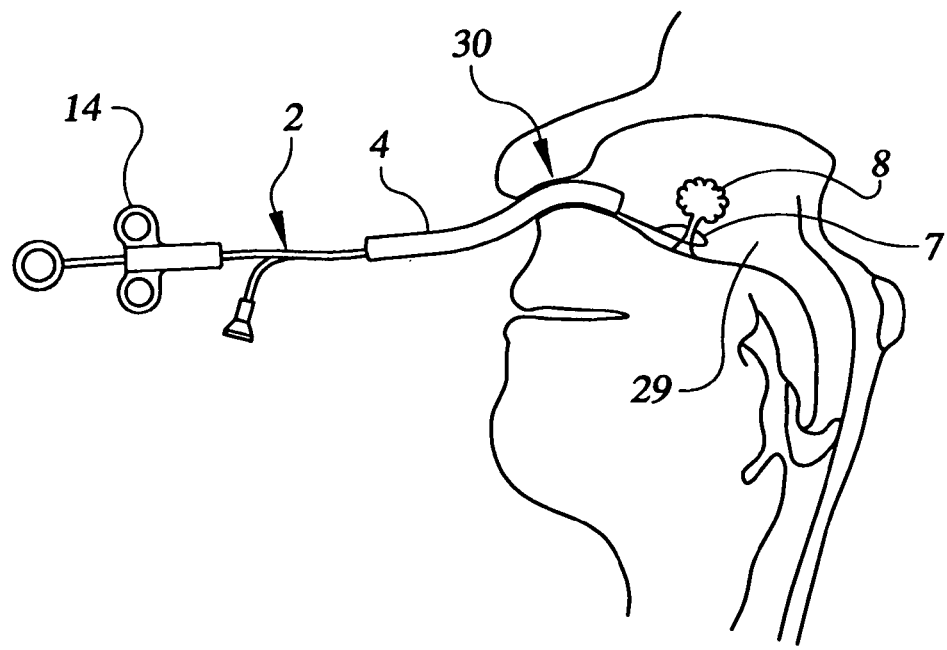
FIG. 4 is an overview of the polypectomy device inserted into a sinus of a patient with the snare wire encircling the base of the polyp.
Figure 5:
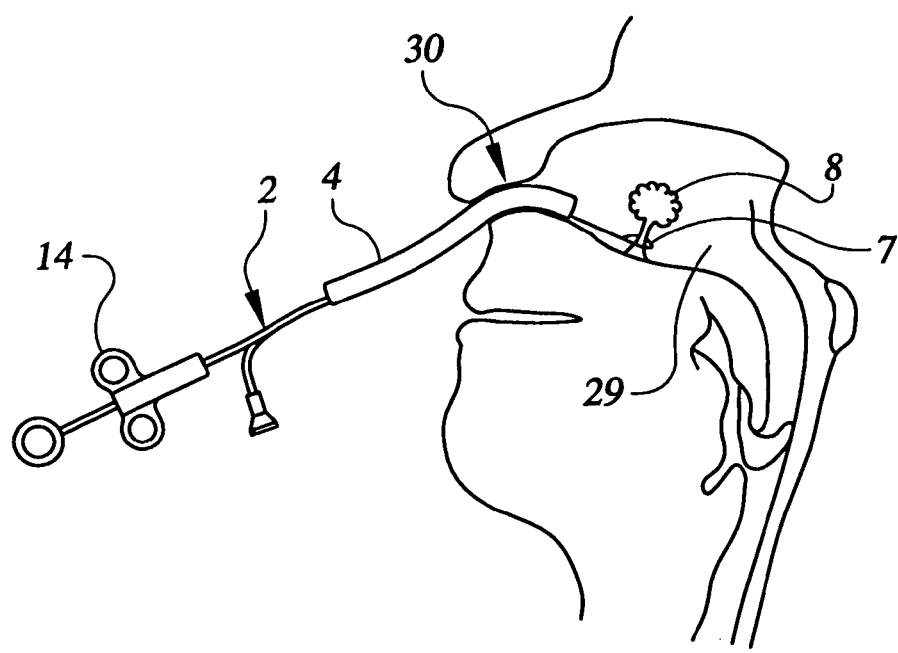
FIG. 5 is a like view with the snare wire pulled proximally to align the jaws of the polypectomy device.

Similarly, as shown in FIG. 4, polyps formed in the nasal sinuses can be removed with the device. A like procedure is followed. An endoscope 4 is inserted into the patient's nasal sinuses 29, through the patient's nostril 30. Once a polyp 8 is located, the polypectomy device 2 is inserted into the endoscope. The snare cable 7 extends to form a hoop which enables the surgeon to capture the polyp. Once the polyp is encompassed by the snare cable, the surgeon activates the cable trigger 14 thereby drawing the snare cable proximally. As shown in FIG. 5, as the surgeon pulls the snare cable proximally, the fixed jaw 5 and the moveable jaw 6 are pulled into place on either side of the polyp 8. As the surgeon further pulls the snare cable, it operates the moveable jaw to draw it toward the fixed jaw, thereby mating the jaws together, or at least bring the jaws into apposition with the polyp stalk caught between them. With the activation of the moveable jaw, the electrical power source is activated, which heats the heating element located on the fixed jaw. The power source is activated by a footswitch (not shown). Thus, as the jaws are held closed, the heating element and the jaws work together to both cut and seal the tissue.

Figure 6:
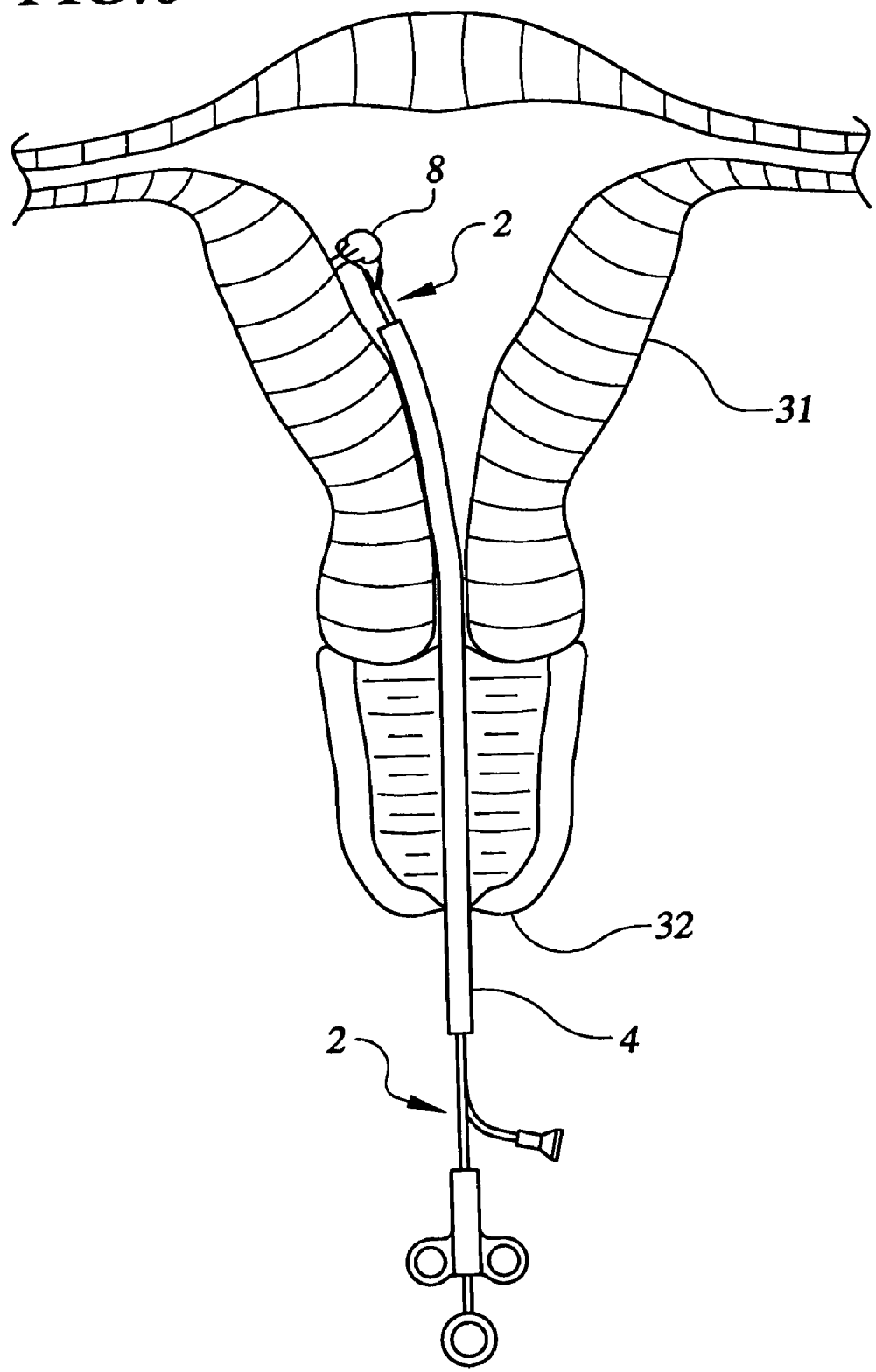
FIG. 6 is an overview of the polypectomy device inserted into the uterus of a patient with the snare wire encircling the base of the polyp.

As illustrated in FIG. 6, polyps in a patient's uterus can be removed with the device. Again, a like procedure is followed. An endoscope 4 is inserted into the patient's uterus 31 through the vagina 32. If a polyp 8 is found, the surgeon inserts the polypectomy device 2 into the working lumen of the endoscope and follows the procedure discussed above.

Similar procedures can be performed in other parts of the body where polyps or other abnormal tissue growth occur, and the examples of colon polyps, sinus polyps, and uterine polyps illustrate the procedure which can readily be adapted to other conditions. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for removing a polyp from the body of a patient, said system comprising:
   an endoscope suitable for performing an endoscopic procedure on the patient; and
   a device for removing polyps, said device comprising:
      a catheter having a proximal end and a distal end;
      a cable trigger operatively connected to the proximal end of the catheter;
      a pair of jaws extending out of the distal end of the catheter; a heating element disposed on at least one of the jaws and located between the pair of jaws;
      a snare cable without the heating element, said snare cable routed through the pair of jaws and operatively connected to the cable trigger; and
      a source of power operably connected to the heating element;
   wherein the device for removing polyps is sized and dimensioned for insertion into the endoscope.

2. The system of claim 1 wherein the heating element is selected from the group consisting of a nichrome wire heating element, a ceramic heating element, an RF heating element, a monopolar electrode heating element and a bipolar electrode heating element.

3. The system of claim 1 wherein:
   the pair of jaws comprises a first jaw and a second jaw;
   the second jaw is rotatable relative to the first jaw; and
   the snare cable is operatively connected to the second jaw and runs from the second jaw to the first jaw and then to the cable trigger.

4. The system of claim 3 further comprising a silicone pad disposed on the grasping face of the second jaw.

5. A method of removing a polyp from the body of a patient, said method comprising the steps of:
   providing a system for removing a polyp from the body of the patient, said system comprising:
      an endoscope suitable for performing an endoscopic procedure on the patient; and
      a device for removing polyps, said device comprising:
         a catheter having a proximal end and a distal end;
         a cable trigger operatively connected to the proximal end of the catheter;
         a pair of jaws extending out of the distal end of the catheter; a heating element disposed on at least one of the jaws and located between the pair of jaws;
         a snare cable routed through the pair of jaws and operatively connected to the cable without the heating element, said snare cable trigger; and
         a source of power operably connected to the heating element;
      wherein the device for removing polyps is sized and dimensioned for insertion into the endoscope;
   inserting the endoscope into the body of the patient and locating the polyp with the endoscope;
   inserting the device for removing polyps into the endoscope such that the distal end of the device for removing polyps is located in the vicinity where the polyp is located;
   extending the snare cable to form a hoop sized and dimensioned to capture the polyp;
   manipulating the hoop to capture the polyp;
   activating the cable trigger to draw the snare cable proximally relative to the catheter and to close the hoop around the polyp;
   pulling the snare cable proximally relative to the catheter to draw the polyp into position between the pair of jaws and to close the pair of jaws upon the polyp; and
   supplying heating power to the heating element to sever the polyp from tissue surrounding the polyp.

6. A method of removing a polyp from the body of a patient, said method comprising the steps of:
   providing a device for removing polyps, said device comprising:
      a catheter having a proximal end and a distal end;
      a cable trigger operatively connected to the proximal end of the catheter;
      a pair of jaws extending out of the distal end of the catheter; a heating element disposed on at least one of the jaws and located between the pair of jaws;
      a snare cable routed through the pair of jaws and operatively connected to the cable without the heating element, said snare cable trigger; and
   placing the distal end of the catheter in the proximity of the polyp;
   pushing the snare cable distally relative to the catheter to open the pair of jaws relative to each other and form a hoop of snare cable extending from the distal end of the catheter;
   manipulating the hoop to engage the polyp;
   pulling the snare cable proximally relative to the catheter to draw the polyp into position between the pair of jaws and to close the pair of jaws upon the polyp; and
   supplying heating power to the heating element to sever the polyp from tissue surrounding the polyp.

* * * * *